(12) United States Patent
Buxton

(10) Patent No.: US 7,678,549 B2
(45) Date of Patent: Mar. 16, 2010

(54) POLYPHENOL INHIBITION OF NUCLEOSIDE DIPHOSPHATE KINASE-B ACTIVITY AND CANCER METASTASIS

(75) Inventor: Iain Buxton, Reno, NV (US)

(73) Assignee: Research Development Foundation, Carson City, NV (US)

(*) Notice: Subject to any disclaimer, the term of this patent is extended or adjusted under 35 U.S.C. 154(b) by 1767 days.

(21) Appl. No.: 10/331,375

(22) Filed: Dec. 30, 2002

(65) Prior Publication Data
US 2003/0175834 A1 Sep. 18, 2003

Related U.S. Application Data

(60) Provisional application No. 60/344,321, filed on Dec. 28, 2001.

(51) Int. Cl.
*A01N 43/16* (2006.01)
(52) U.S. Cl. .................. 435/7.23; 514/453
(58) Field of Classification Search ............ 514/456, 514/453
See application file for complete search history.

(56) References Cited

U.S. PATENT DOCUMENTS 6,248,341 B1 * 6/2001 Anderson et al. .......... 424/401

FOREIGN PATENT DOCUMENTS

| WO | WO 00/47193 | 8/2000 |
| WO | WO 00/52467 | 9/2000 |
| WO | WO 0057875 A1 * | 10/2000 |

OTHER PUBLICATIONS

Ho et al. (Toxicological and Environmental Chemistry 1999; 69: 509-519).*
Boukharta et al. (Nutrition and Cancer 1992; 18: 181-189).*
Castonguay et al (International Journal of Oncology 1997; 10: 367-373).*
Anciaux, K. et al. Inhibition of Nucleoside Diphosphate Kinase (NDPK/nm23) by cAMP analogues: *Federation of European Biochemical Societies*, 1997, pp. 75-79.
Malmquiest NA, et al. Ellagic Acid Inhibits Nucleoside Diphosphate Kinase-B Activity: *Proc West Pharmacol Soc.*, 2001, vol. 44, pp. 44-57-44-9, Abstract Only.
Biondi, R. M. et al. Inhibition of Nucleoside Diphosphate Kinase Activity by in Vitor Phosphorylation by Protein Kinase CK2/ Differential Phosphorylation of NDP Kinases in HeLa Cells in Culture: *Federation of European Biochemical Societies*, 1996, pp. 193-187.
Valenti, D. et al. Inhibition of Nucleoside Diphosphate Kinase in Rat Liver Mitochondria by Added 3'-azido-3'-deoxythymidine: *Federation of European Biochemical Societies*, 1999, pp. 291-295.
Odagaki, Y. et al. Receptor-mediated and Receptor-Independent Activation of G-Proteins in Rat Brain Membranes: *Life Science*, 1998, vol. 62(17-18), pp. 1537-1541.
Anzinger et al., "Secretion of a nucleoside diphosphate kinase (Nm23-H2) by cells from human breast, colon, pancreas and lung tumors," *Proc. Western Pharm. Soc.*, 44:61-63, 2001.
Buxton et al., "Evidence supporting the nucleotide axis hypothesis: atp release and metabolism by coronary endothelium," *American Journal of Physiology, Heart and Circulatory Physiology*, 281:H1657-H1666, 2001.
Hamby et al., "Expression of a catalytically inactive H118Y mutant of nm23-h2 suppresses the metastatic potential of line iv cl 1 human melanoma cells," *Int. J. Cancer*, 88:547-553, 2000.
Hudson et al., "A role fo rthe nm23 gene product in human breast cancer metastasis," *J. of Investigative Medicine*, 44:164A, 1996.
Satterwhite et al., "Human breast cancer cells in culture express a nucleoside diphosphate kinase and generate extracellular atp," *FASEB Journal*, 12:A441, 1998.

* cited by examiner

*Primary Examiner*—Brandon J Fetterolf
(74) *Attorney, Agent, or Firm*—Fulbright & Jaworski, L.L.P.

(57) ABSTRACT

Aggressive human tumor cells from disparate tissues were found to secrete nucleoside diphosphate kinase-B (NDPK-B) as a phosphoprotein into the extracellular environment. The secreted enzyme was capable of trasphosphorylation activity in the absence of a phosphoryl donor, thereby producing elevated level of extracellular ATP that plays a significant role in angiogenesis required for the growth of cancer cells and cancer metastasis. A series of structurally related non-nucleotide anticancer compounds such as ellagic acid (EA), epigallocatechin gallate (EGCG), and epicatechin gallate (ECG) were found to inhibit the activity of secreted nucleoside diphosphate kinase-B as well as angiogenesis. The nucleoside diphosphate kinase-B inhibition data disclosed herein can be used in predicative models to design novel inhibitors of nucleoside diphosphate kinase-B activity.

5 Claims, 11 Drawing Sheets

STS                    STS

Cyclodextrin 5mM            Filipin III 1ug/ml

POLYPHENOL INHIBITION OF NUCLEOSIDE DIPHOSPHATE KINASE-B ACTIVITY AND CANCER METASTASIS

CROSS-REFERENCE TO RELATED APPLICATION

This non-provisional patent application claims benefit of provisional patent applications U.S. Ser. No. 60/344,321, filed Dec. 28, 2001.

BACKGROUND OF THE INVENTION

1. Field of the Invention

The present invention relates generally to the fields of pharmacology and tumor biology. More specifically, the present invention relates to secretion of nucleoside diphosphate kinase (NDPK) from human tumors and the effects of inhibiting nucleoside diphosphate kinase activities.

2. Description of the Related Art

Cancer is the second leading cause of death in the United States, with one in four deaths attributed to the disease. Patients that succumb to breast cancer do so from the formation of metastatic tumors. Indeed, deaths due to colon, pancreatic, lung and other cancers are most often the result of metastatic disease rather than the consequence of the primary tumor per se (1).

Metastasis is a complex set of biological events involving proteolysis, cell motility, intravasation and extravasation, cellular communication, angiogenesis, and tumor growth. A great deal of recent interest has developed surrounding the need for metastatic tumors to develop blood supply from the host in order to grow and that on this basis, new cancer therapy can be developed (2).

The so-called metastasis suppressor gene, Nm23, may be an integral mediator involved in one or more of the events of metastasis. The description of the first human Nm23 gene (3) as a homologue of a *Drosophila* gene involved in the formation of the wing disk indicated a potential for metastasis inhibition and several studies have supported this claim.

Four Nm23 genes are encoded in human cells, with the two most highly studied being Nm23-H1 and Nm23-H2, encoding nucleoside diphosphate kinase-A (NDPK-A) and nucleoside diphosphate kinase-B (NDPK-B) respectively. Each of these enzymes, known to form homo-hexamers of 17.5 kDa (Nm23-H1) and 21.5 kDa (Nm23-H2) monomers, function primarily as a nucleoside diphosphate kinase (NDPK) in maintaining intracellular "housekeeping" by nonspecific trans-phosphorylation, and have later been found to have DNA binding activity and other non-nucleoside diphosphate kinase activities (4-7).

The enzymatic properties of the nucleoside diphosphate kinase are curious as these enzymes will bind a wide variety of both purine and pyrimidine triphosphates as phosphoryl donor and substrate. These enzymes, in the presence of divalent cations, covalently transfer the terminal γ-phosphate of a nucleoside triphosphate (NTP) to a nucleoside diphosphate (NDP) via a high-energy phosphohistidine intermediate: $N_1DP+N_2TP \Leftrightarrow N_1TP+N_2DP$. The promiscuous nature of the enzyme may subserve its ability to act as a transphosphorylase transferring ATP from one cellular compartment to another.

It has been reported that nucleotides, particularly ATP derived from endothelial cells, are regulators of regional blood flow (8). Hence, it is hypothesized that there is a role for tumor-derived Nm23 in events supporting metastasis, particularly those of intravasation and extravasation of tumor cells that would be supported by the extracellular actions of nucleotides. The present invention provides evidences that support this hypothesis and further shows that inhibition of nucleoside diphosphate kinase activity may result in suppression of metastasis.

SUMMARY OF THE INVENTION

The present invention provides data that indicate nucleoside diphosphate kinase-B was secreted as a phosphoprotein into the extracellular environment by a variety of human tumors (e.g. breast, lung, colon, and prostate cancer cells). Localized production of extracellular ATP generated by tumor-derived nucleoside diphosphate kinase-B may induce tumor cell intravasation into capillary vessels, transit and extravasation at a distant site and as such, these events may be altered by blockade of this enzyme. Accordingly, the present invention further shows that a series of structurally related non-nucleotide anticancer compounds such as ellagic acid (EA), epigallocatechin gallate (EGCG), and epicatechin gallate (ECG) inhibit the activity of secreted nucleoside diphosphate kinase-B as well as angiogenesis. The anti-nucleoside diphosphate kinase property reported here suggests a novel mechanism by which these compounds may be anti-tumorigenic.

In one embodiment of the present invention, there is provided a method of screening for a compound that inhibits tumor cell angiogenesis, comprising the step of: determining the activity of nucleoside diphosphate kinase-B in the presence or absence of said compound, wherein a decrease of nucleoside diphosphate kinase-B activity in the presence of said compound indicates said compound would inhibits tumor cell angiogenesis.

In another embodiment of the present invention, there is provided a method of inhibiting tumor cell angiogenesis, comprising the step of: contacting said cell with an inhibitor of the activity of nucleoside diphosphate kinase-B. Representative examples of nucleoside diphosphate kinase-B inhibitors include ellagic acid (EA), epigallocatechin gallate (EGCG), and epicatechin gallate (ECG).

In another embodiment of the present invention, there is provided a method of inhibiting activity of nucleoside diphosphate kinase-B in a tumor cell. This method comprises the step of contacting the cell with ellagic acid (EA) or a structurally similar analogue, epigallocatechin gallate (EGCG) or a structurally similar analogue, or epicatechin gallate (ECG) or a structurally similar analogue.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
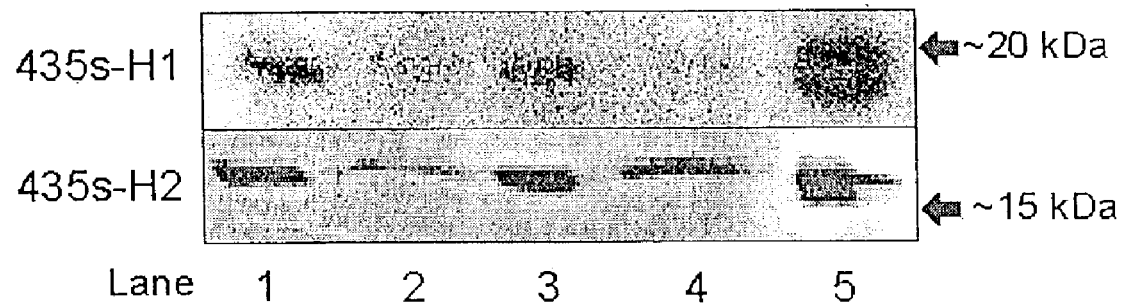
FIG. 1 shows Western blot analysis of Nm23 isoforms of breast cancer cells. Cell homogenates and conditioned incubation buffer were prepared and fractionated as described and separated by gel electrophoresis followed by blotting proteins to membranes. Westerns were probed with antibodies specific for Nm23-H1 and Nm23-H2 isoforms and developed using the alkaline phosphatase method. Lane 1, whole cell homogenate; Lane 2, membrane fraction; Lane 3, cytosolic fraction; Lane 4, secreted fraction; Lane 5, standard nucleoside diphosphate kinase from rat liver (Sigma). Data are representative of numerous experiments with these and other tumor cell lines.

In the methods of the present invention, aggressive human tumor cells from disparate tissues were found to secrete nucleoside diphosphate kinase-B (NDPK-B) into the extracellular environment. The enzyme was secreted as a phosphoprotein and was capable of trasphosphorylation activity in the absence of a phosphoryl donor. This activity could serve as a mechanism for producing elevated extracellular ATP that is particularly useful in the setting of angiogenesis required for the growth of cancer cells and cancer metastasis. Localized production of extracellular ATP generated by tumor-derived nucleoside diphosphate kinase-B would induce tumor cell intravasation into capillary vessels, transit and extravasation at a distant site and as such, these events may be altered by blockade of this enzyme.

Nucleoside diphosphate kinase-B secretion from human tumor cells and its action to produce ATP extracellularly lead one to believe that the hypothesis of Nm23 gene expression being directly correlated with low metastasis potential is an incomplete assessment. The present invention demonstrates that a series of structurally related non-nucleotide compounds, i.e., ellagic acid (EA), epigallocatechin gallate (EGCG), and epicatechin gallate (ECG), that have been proposed as anticancer agents inhibit the secreted nucleoside diphosphate kinase-B as well as angiogenesis. The fact that a number of compounds that are touted as chemopreventative agents inhibit nucleoside diphosphate kinase activity could further implicate extracellular nucleotides in the metastatic process and there are reports of tumoregenesis studies that contradict the original claims of non-metastatic potential now ascribed to Nm23. The nucleoside diphosphate kinase-B inhibition data disclosed herein can be used in predicative models to design novel inhibitors of nucleoside diphosphate kinase-B activity. Ultimately, novel potent nucleoside diphosphate kinase-B inhibitors can be tested in in vivo whole tumor growth and angiogenesis experiments.

The present invention is directed to a method of screening for a compound that inhibits tumor cell angiogenesis, comprising the step of: determining the activity of nucleoside diphosphate kinase-B (NDPK-B) in the presence or absence of said compound, wherein a decrease of nucleoside diphosphate kinase-B activity in the presence of said compound indicates said compound would inhibits tumor cell angiogenesis.

The present invention is also directed to a method of inhibiting tumor cell angiogenesis, comprising the step of: contacting said cell with an inhibitor of the activity of nucleoside diphosphate kinase-B. Representative examples of nucleoside diphosphate kinase-B inhibitors include ellagic acid (EA), epigallocatechin gallate (EGCG), and epicatechin gallate (ECG).

The present invention is also directed to a method of inhibiting activity of nucleoside diphosphate kinase-B in a tumor cell. This method comprises the step of contacting the cell with ellagic acid (EA) or a structurally similar analogue, epigallocatechin gallate (EGCG) or a structurally similar analogue, or epicatechin gallate (ECG) or a structurally similar analogue.

The following examples are given for the purpose of illustrating various embodiments of the invention and are not meant to limit the present invention in any fashion.

EXAMPLE 1

Production of NDPK-B

The human tumors MDA-MB-435s (breast ductal carcinoma), Calu-1 (metastatic lung carcinoma), WiDr (colorectal carcinoma), and PC-3 (prostatic carcinoma) were grown to confluence in DMEM with 10% heat-inactivated FBS and antibiotics. Media was replaced with Krebs buffer (25 mM Hepes, pH 7.4) and incubated at 37° C. with gentle rocking for 4 hours. The supernatant was removed and concentrated by spin concentrators. Nucleoside diphosphate kinase activity of the retentate was assayed for activity and stored at −20° C.

EXAMPLE 2

Western Blot

Human breast cancer cells were grown to confluence, scraped from dishes and homogenized in standard buffers containing protease inhibitors. Membranes were prepared by differential centrifugation first at 10,000×g for 5 min to remove nuclei and then at 48,000×g for 30 min to recover cell soluble and particulate fractions. Samples were boiled in SDS sample buffer, separated by PAGE on 12% gels, blotted to PDVF and probed for Nm23 isoforms using commercially available antibodies (US Biological, MA).

EXAMPLE 3

Detemination of Nm23-H2 Phosphoprotein

Breast cancer cells (435s) were grown to confluence and labeled with [$^{32}$P]-orthophosphate (100 µCi/$10^7$ cells) overnight. Radioactivity was then determined using scintillation in total protein by acid precipitation and in the concentrated Nm23 fraction following concentration. Counts associated with Nm23-H2 were confirmed using autoradiography. Nm23-H2 phosphoprotein was then incubated with ADP in the absence of a phosphoryl donor.

EXAMPLE 4

NDPK-B Kinase Activity Assay

Conversion of ADP to ATP, using GTP as the phosphoryl donor, was quantified using the Luciferin-Luciferase ATP assay as we have previously described (9). All necessary steps were taken to eliminate and account for interference between potential nucleoside diphosphate kinase-B inhibitors and the luciferase in the assay.

EXAMPLE 5

Angiogenesis Assay

Fluorescence activated cell sorting (FACS) was used to select cardiac endothelial cells positive for the PECAM marker CD31. Endothelial cells were plated on a matrix of basement proteins from the Engelbreth Holm-Swarm (EHS) mouse tumor. A complete DME media containing 10% FBS was used to maintain endothelial cultures. Differentiation of the cells into endothelial tubes was monitored in the presence and absence of the compounds of interest.

EXAMPLE 6

Secretion Of Nucleoside Diphosphate Kinase By Human Tumor Cells

Both Nm23-H1 and -H2 genes were expressed in breast cancer cells, and the nucleoside diphosphate kinase secreted from the MDA-MB-435s breast cancer cells was the Nm23-H2 isoform (FIG. 1). While both H1 and H2 isoforms were readily detected with specific antibodies, only the H2 protein was found in the incubation medium surrounding cells.

Figure 2:
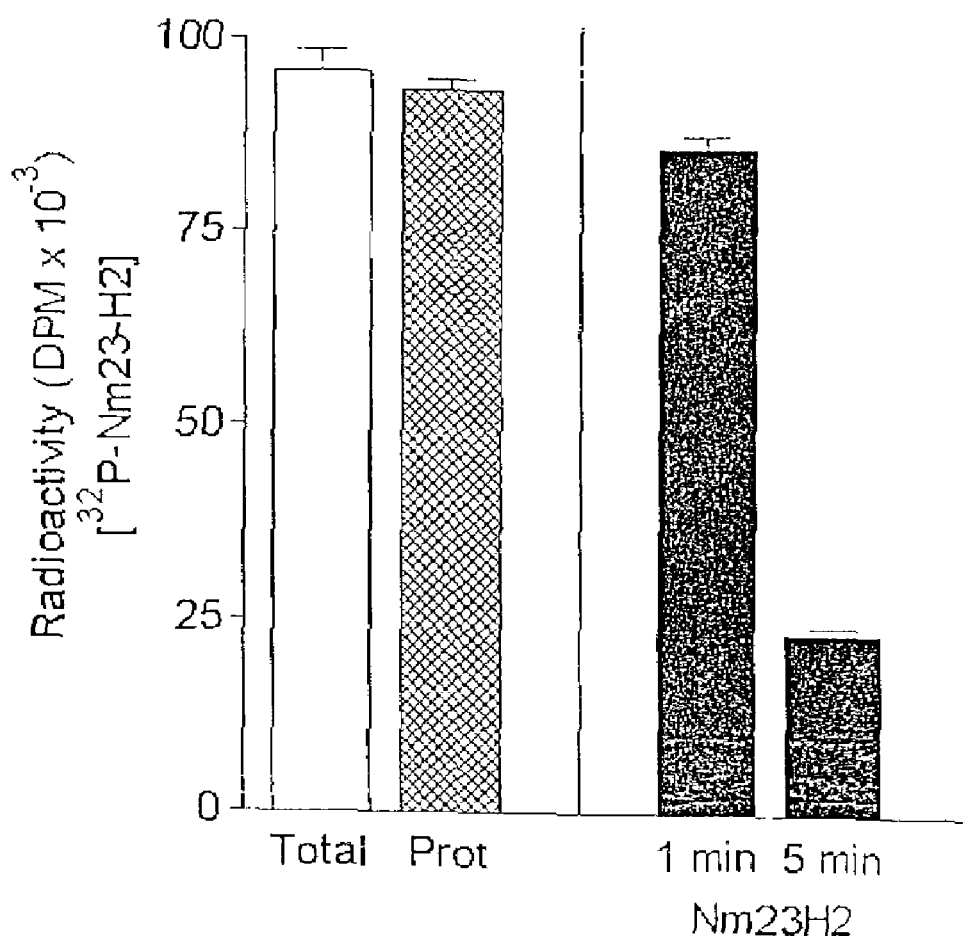
FIG. 2 shows Nm23-H2 is a secreted nucleoside diphosphate kinase. The incubation buffer was sampled from four different tumor cell types and the nucleoside diphosphate kinase activity was assessed enzymatically in the presence of excess GTP (1 mM) by measuring the production of ATP production using the luciferin-luciferase assay. Relative luminescence units (RLU) were corrected from background and converted to ATP by comparison to a standard curve. Data are presented as mean ±SEM, n=3. Nm23-H2 substrate affinities ($K_M$) for ADP in disparate tumors are not significantly different while the apparent Vmax suggests distinctions. The average Nm23-H2 $K_M$ from all sources is (21.59+/−2.49 uM).

In order to determine whether Nm23-H2 is secreted from cancer cells that are highly metastatic and form solid tumors at distant sites, the abilities of other cultures of cancer cells to secrete Nm23-H2 were examined. All metastatic human tumors studied secreted nucleoside diphosphate kinase-B isoform with similar affinities for the substrate ADP (21.59+/−2.49 µM SEM), suggesting that the ability to secrete nucleoside diphosphate kinase is a property of transformed cells (FIG. 2). Control experiments with normal cells did not result in secretion of Nm23 proteins (data not shown).

Because Nm23-H2 was secreted from tumor cells in culture, it was determined whether the secreted Nm23-H2 requires the presence of a phosphoryl donor outside the cell to generate extracellular NTP, or if the protein is secreted in a phosphorylated form.

Figure 3:
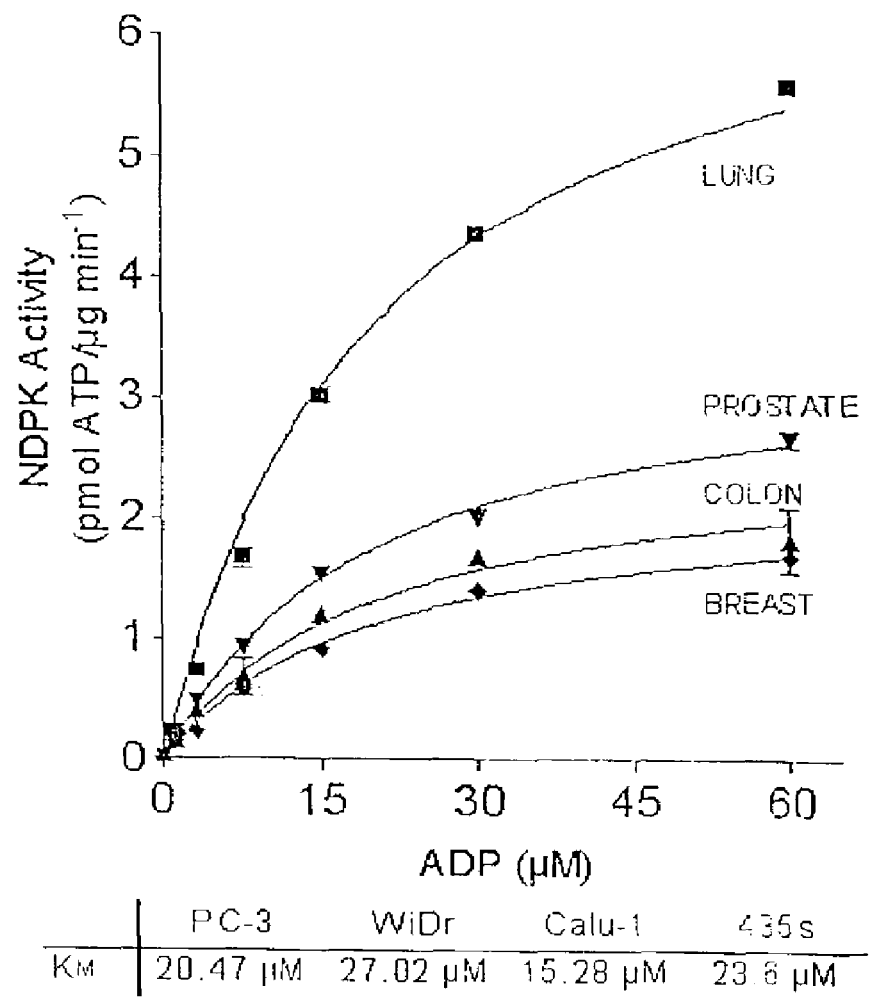
FIG. 3 shows detection of secreted Nm23-H2 as a phosphoprotein. [$^{32}$P]-labeled cells were allowed to condition incubation buffer, which was collected, concentrated and used to determine [$^{32}$P] incorporation by radioactive scintillation counting. Radioactivity in the buffer collected (Total) and in total protein (Prot) were determined by acid precipitation followed by scintillation counting. Nm23-H2 radioactivity was confirmed by autoradiography and found to account for the majority of radioactivity in secreted protein. ADP was added as a phosphoryl acceptor at 100 µM for 1 and 5 min. Data are Mean ±SEM of duplicate determinations in three experiments.

Nm23-H2 was secreted as a phosphoprotein (FIG. 3) and that the phosphate was transferred to substrate (ADP) as expected for a nucleoside diphosphate kinase. In agreement with the pig-pong transphosphorylase activity previously described for this enzyme, the loss of radioactivity from Nm23-H2 was time dependent in the presence of phosphate acceptor (FIG. 3).

In summary, human breast, colon, lung and prostate tumor cells all expressed secreted nucleoside diphosphate kinase-B activity (FIG. 2). These cancer cells may translate Nm23-H2 as both an ecto-nucleoside diphosphate kinase and exo-nucleoside diphosphate kinase-B enzyme. Western blots showed that the -H2 isoform was found in the membrane of the breast cancer cell but this may be due to its staging there for secretion. Nm23-H2 was secreted by cells as a phosphoprotein. This experimental data suggests that the enzyme is able to transfer a phosphoryl group from a nucleoside triphosphate donor within the cell to a histidine in the protein and retain this phosphorylation until outside the cell where the enzyme can phosphorylate a nucleoside diphosphate.

The phosphohistidine (ping-pong) transphosphorylase mechanism is well known for nucleoside diphosphate kinases and while such a reaction scheme may seem awkward as one nucleoside triphosphate is hydrolyzed in favor of another, the net gain is a clear benefit to tumor biology as it puts the nucleoside triphosphate outside the cell. Since the enzyme is secreted as a phosphoprotein it is capable of transphosphorylation activity in the absence of an extracellular phosphoryl donor. This activity may be a mechanism for producing elevated extracellular ATP, particularly in the setting of apoptosis of tumor cells and angiogenesis required for tumor growth.

EXAMPLE 7

Inhibition of Nucleoside Diphosphate Kinase Activity

Localized production of extracellular ATP by tumor derived nucleoside diphosphate kinase-B may facilitate the process of metastasis as it may support tumor cell transit, intravasation and angiogenesis. Therefore, inhibitors of nucleoside diphosphate kinase-B may have suppressive effects on tumor metastasis.

It was immediately evident that no specific, potent inhibitors for nucleoside diphosphate kinases were known. Thus search for nucleoside diphosphate kinase-B inhibitors began by examining compounds that had been described as having anti-angiogenesis or general anti-cancer properties. As inhibitor data was gathered, subsequent compounds can be chosen based on conserved structural motifs found in the most potent inhibitors.

The compounds selected for the present study were chosen for a variety of reasons. The polyphenolic tea compounds such as theaflavins, epigallocatechin gallate (EGCG), epicatechin gallate (ECG) and epigallocatechin are known to suppress cancer cell proliferation, inhibit angiogenesis and invasion into MATRIGEL®. Ellagic acid was originally identified through structure search based on the apparent importance of the gallate moiety contained in the most potent polyphenolic tea compounds and was later found to be reported as a potential chemopreventative agent. Piceatannol, resveratrol, genestein, and silymarin are also polyphenolic compounds found to possess anticarcinogenic properties via a variety of proposed mechanisms including inhibition of COX and LOX pathways. They were also chosen because of conserved structural motifs between them and the tea compounds. Purpurogallin was originally studied as a potential inhibitor of oncogene product enzyme activity. The nucleoside analogs AZT, PAPS, and 8-Cl-cAMP were chosen as potential nucleoside diphosphate kinase-B inhibitors because of their previously reported inhibition of nucleoside diphosphate kinases in relation to their anti-HIV properties and because their relatively high $K_1$s could be compared to more promising compounds.

Results in Table 1 shows that nucleoside diphosphate kinase-B activity was inhibited by the polyphenolic constituents of tea (epigallocatechin gallate, epigallocatechin, and the theaflavins). Nucleoside analogs 8-Cl-cAMP and PAPS also inhibited nucleoside diphosphate kinase-B transphosphorylation activity but with relatively low potency (Table 1). The compound ellagic acid (hexahydroxydiphenic acid dilactone), found through a structure search based on the conserved moiety contained in the polyphenolic tea compounds, had the highest inhibitory effect on nucleoside diphosphate kinase-B among the compounds tested (Table 1).

TABLE 1

Inhibitors Of NDPK-B Activity

| Compd. | Inhibition | Conc. tested | $IC_{50}$ | Inhibition type | $K_{M(ADP)}$ |
|---|---|---|---|---|---|
| EGCG | Yes | 3-700 µM | 150 µM | NC | 9.7 ± 1.8 |
| ECG | Yes | 3-700 µM | 170 µM | NC | 13.3 ± 1.7 |
| EGC | No | 3-700 µM | — | — | — |
| Black tea Extract | Yes | 0.7-300 µM | 80 µM | NC | 11.3 ± 2.7 |
| Piceatannol | No | 1-1000 µM | — | — | — |
| Resveratrol | No | 1-1000 µM | — | — | — |
| Genestein | No | 0.3-30 µM | — | — | — |
| Silmarin | No | 3-1000 µM | — | — | — |
| Purpurogallin | Yes | 1-300 µM | 600 µM | NC | 20.4 ± 3.5 |
| AZT | No | 0.3-100 µM | — | — | — |
| PAPS | Yes | 10-1,000 µM | 500 µM | NC | 7.1 ± 1.4 |
| 8-Cl-cAMP | Yes | 3-10,000 µM | 1 mM | NC | 7.5 ± 1.5 |
| Ellagic Acid | Yes | 1-300 µM | 23 µM | NC | 18.8 ± 2.7 |

Partially purified tumor cell-secreted nucleoside diphosphate kinase-B was incubated with ADP and GTP in the presence of varying concentrations of putative nucleoside diphosphate kinase inhibitors or putative metastasis/angiogenesis inhibitors and the resulting ATP generated was measured by chemiluminescence using the luciferin-luciferase assay. All compounds found to inhibit nucleoside diphosphate kinase-B did so by depressing the $V_{max}$ of the enzyme while maintaining a statistically similar $K_M$, suggesting noncompetitive inhibition with respect to phosphoryl donor (GTP). Molecular modeling studies support these kinetic assumptions (data not shown).

Figure 4:
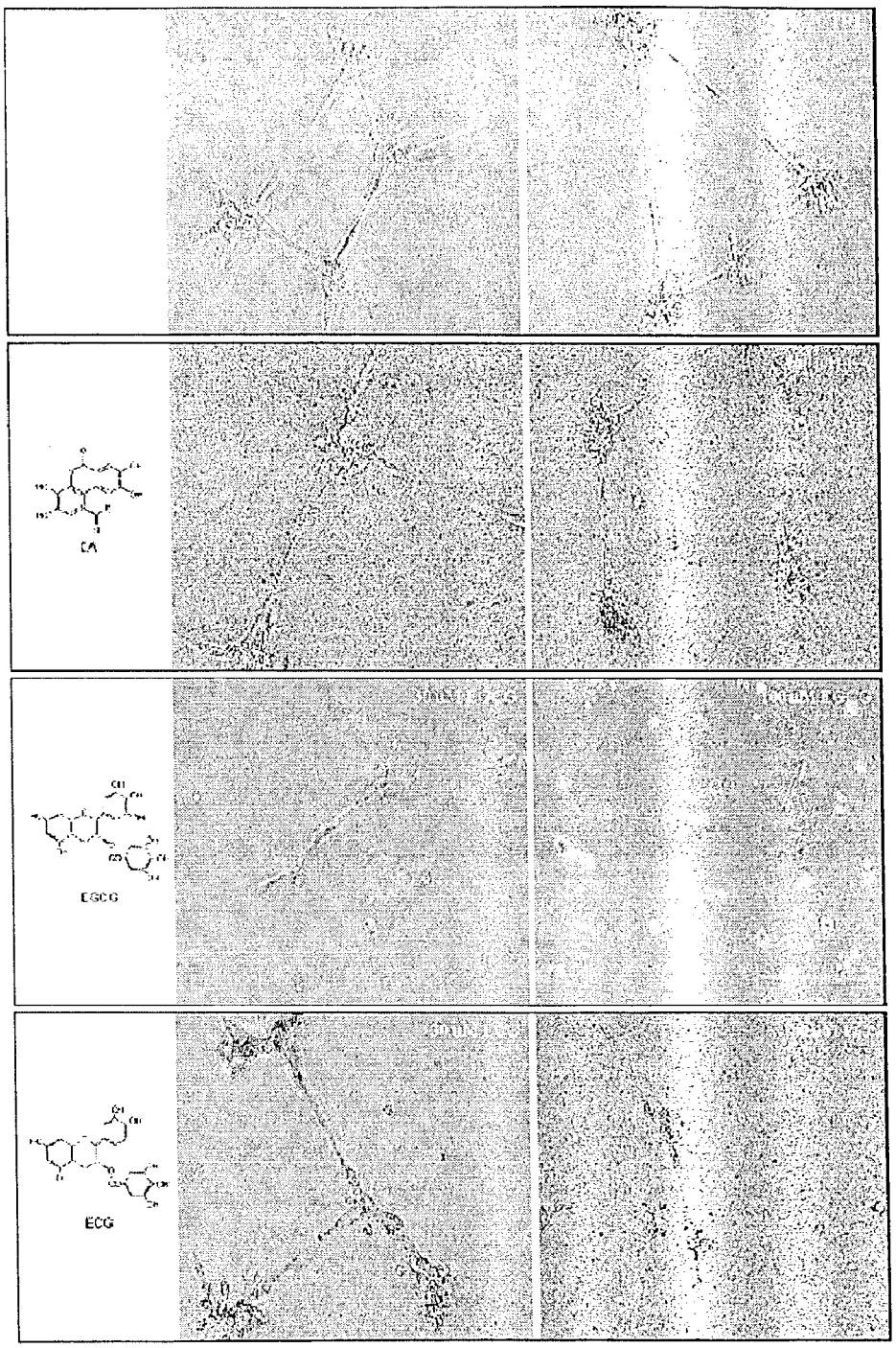
FIG. 4 shows inhibition of angiogenesis. Endothelial cells (CD31$^+$ cells from guinea pig hearts) were plated on a matrix composed of basement proteins from the Engelbreth Holm-Swarm (EHS) mouse tumor. The cells were incubated for ~16 hrs in Complete Dulbecco's Modified Eagle Medium (CD-MEM) with added tea catechins ellagic acid (EA), epigallocatechin gallate (EGCG), and epicatechin gallate (ECG). Bright field images were taken using a Nikon phase-contrast microscope and a Pulnix digital camera. Image sharpening was achieved with Imagemaster and Adobe Photoshop software. Data are representative of two experiments.

Epicatechin gallate (ECG), epigallocatechin gallate (EGCG), and ellagic acid (EA) were also used at 30 and 100 µM to determine their effect on angiogenesis (FIG. 4). Each of the nucleoside diphosphate kinase inhibitors tested produced a dose-dependent inhibition of angiogenesis consistent with a role for ATP in supporting angiogenesis.

In conclusion, several compounds reported to possess anti-angiogenic or anti-tumorigenic properties inhibit nucleoside diphosphate kinase-B activity. Indeed, a trend was found where compounds with more thoroughly described mechanisms of anti-tumorigenicity tended to inhibit nucleoside diphosphate kinase-B activity less or not at all while compounds with poorly described mechanisms of anti-tumorigenicity tended to inhibit nucleoside diphosphate kinase-B activity potently. The anti-nucleoside diphosphate kinase property reported here suggests a novel mechanism by which these compounds may be anti-tumorigenic. Taken together, these findings suggest that inhibition of nucleoside diphosphate kinase-B activity is mechanistically associated with inhibition of metastasis by cancer cells. Ellagic acid, along with the other potent nucleoside diphosphate kinase inhibitors, will provide the necessary data for future predictive studies aimed at the design of novel nucleoside diphosphate kinase-B inhibitors.

EXAMPLE 8

Role of Ecto-ATP Generation in Breast Cancer Metastasis

Endothelial cell apoptosis may play a key role in the development of new blood vessel growth during angiogenesis related to metastatic tumor development. Apoptosis can be initiated through intrinsic factors that promote an internal program of self-destruction or via numerous extrinsic signals. Most notably, reactive oxygen species (ROS) appear to have functional significance in initiating or transducing cell death. Many studies have shown that whether delivered exogenously or through production by pro-inflammatory factors, ROS promote apoptosis in endothelial cells. Regardless of the origin of the signal, apoptotic mechanisms involve an elaborate and well-conserved cascade of signal transduction pathways.

A crucial element of the apoptotic pathway is the activation of caspases. These cysteinyl aspartic acid-directed proteases are triggered in a multi-tiered fashion with upstream enzymes (initiators) cleaving and thereby activating downstream caspases (effectors). The activation of the effectors such as caspase-3 is a common event signaled by many different stimuli. Membrane delimited caspase-3 regulation in endothelial cells is required for the angiogenic response to metastasis in breast cancer. Apoptotic signaling can begin at the plasma membrane or within intracellular organelles such as mitochondria. Microdomains at the plasma membrane provide a mechanism for specificity and efficiency of metastasis-mediated signaling of new vessel growth. A subset of these microdomains, caveolae, appears as flask shaped invaginations on the plasma membrane of many cells including endothelium. Caveolae contain the integral membrane protein caveolin and are rich in cholesterol and sphingomyelin. The latter properties impart low-density buoyancy when compared to other regions of the plasma membrane. This characteristic is used to isolate caveolae from the plasma membrane by flotation on density gradients. The enrichment of caveolin in these preparations is used as a marker for the successful isolation of caveolae. While the identification of other signaling proteins purified with these fractions does not necessarily imply functional significance, this finding is suggestive of such a relationship. In support this notion, apoptosis induced via tumor necrosis factor-α (TNF-α) has been shown to be dependent on intact caveolae and the TNF receptor co-localizes with caveolar domains. This implies localization of the signaling milieu necessary for transduction of the originating stimulus.

While most reports demonstrate that pro-caspase-3 is primarily a cytoplasmic protein, Mancini, et al. reports the discovery of pro-caspase-3 at the mitochondrial inner membrane. More recently, Krebs, et al. describe purification of pro-caspase-3 in a heavy-membrane preparation. This is in stark contrast to the report of a low-density membrane caspase-3 isolation that suggests a unique localization of an "executioner" caspase to the plasma membrane in endothelial cells. Caspase-3 localized in caveolae may allow for targeting of membrane-bound substrates to the proteolytic enzyme in the angiogenic response to metastasis.

A endothelial model was developed with the use of fluorescence activated cell sorting and antibodies or lectins directed against proteins located on the extracellular surface. These cells have the ability of to retain an endothelial-like phenotype when cultured on collagen-treated plastic. An executioner enzyme, caspase-3, is localized at the plasmalemmal surface in close proximity to caveolin-1.

EXAMPLE 9

Results

Figure 5:
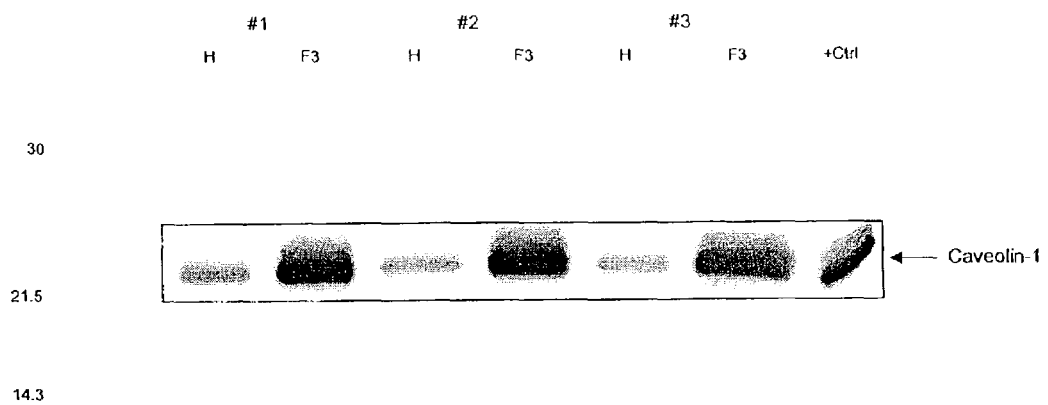
FIG. 5 shows a Western blot analysis of insoluble, low-density fractions from whole cell lysates prepared from three separate cell isolation procedures. "H" is the sonicated whole cell lysate which is layered at the bottom of the discontinuous gradient. "F3" is the third 1.5 ml fraction of the 12 ml gradient. The positive control is a human endothelial lysate.

Western blot analysis demonstrates an enhancement of caveolin staining relative to the starting cellular homogenate (FIG. 5). This caveolin-containing layer is routinely found at the interface between the 6% and 36% layers and can be easily identified by the appearance of a flocculent, light-scattering band. The enrichment of caveolin-1 indicates the successful separation and concentration of caveolae from the whole cell lysate.

Figure 6:
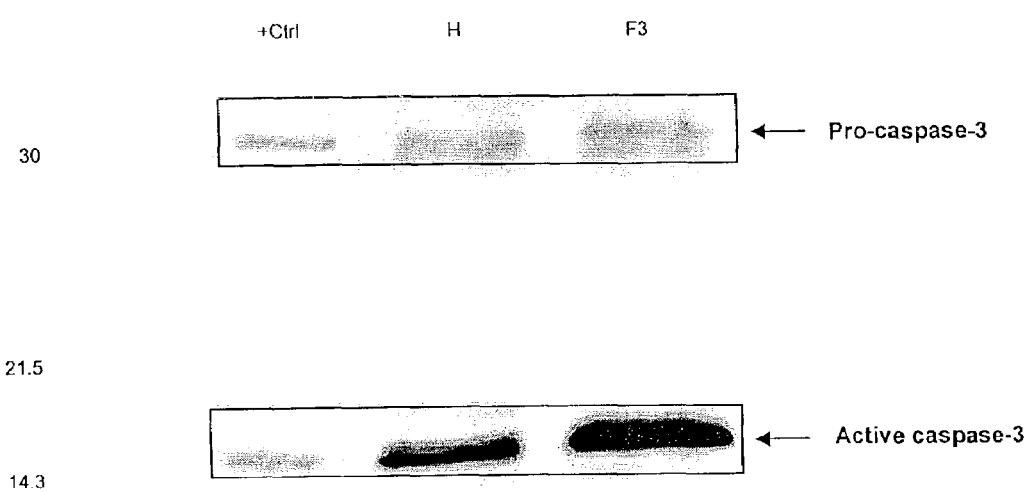
FIG. 6 shows a Western blot analysis of insoluble, low-density fractions from whole cell lysates. Caspase-3 enrichment is routinely found in the same fraction as caveolin-1 indicated by "F3". "H" is the sonicated whole cell lysate which is layered at the bottom of the discontinuous gradient. The positive control is a human lymphoma cell lysate.
Figure 7:
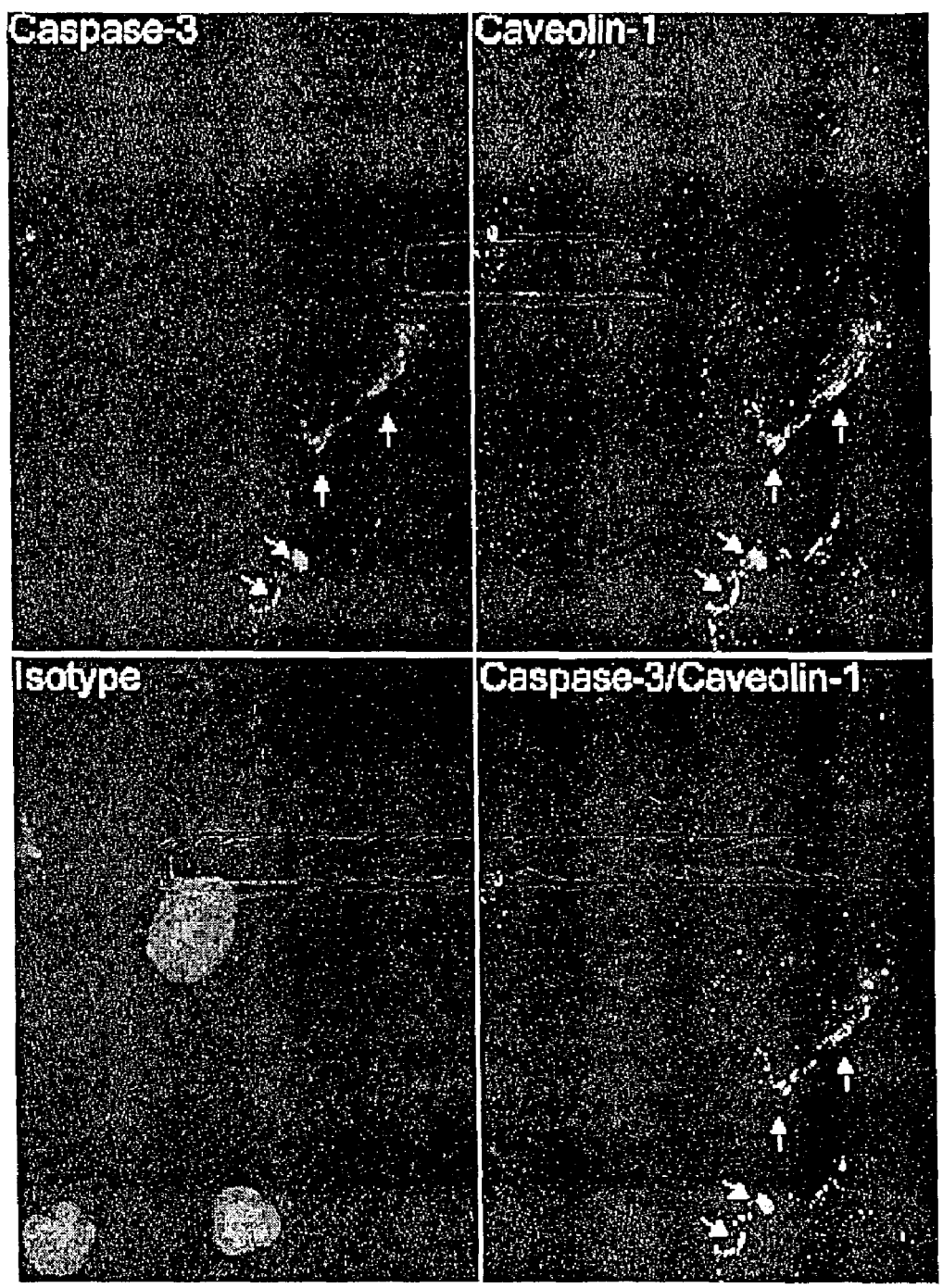
FIG. 7 shows immunofluorescent images of endothelial cells stained with anti-caveolin-1 (green) document the presence and location of caveolae, anti-caspase-3 (red) to show the presence of the caspase-3 enzyme and, & Hoechst 33342 (blue) to mark the presence of the cell nucleus. Fifty 0.4 micron Z-series steps were obtained in each color channel using a digital camera mounted on a research microscope. The resulting images were reconstructed using a three image nearest neighbor deconvolution algorithm. The deconvoluted images were overlaid at a 50-50 ratio. Yellow indicates areas of co-localization.

The enrichment for caspase-3 relative to starting homogenate is found in the same low density fraction where caspase-3 (32 kDa) and its 17 kDa active fragment is evident (FIG. 6). Co-localization of caveolin-1 with caspase-3 is evidenced by immunofluorescence microscopy in fixed and permeablized GPCEC (FIG. 7).

Caveolin-1 staining is concentrated at the plasmalemmal border (upper, left panel). A similar staining pattern is noted for caspase-3 (upper, right panel). Simultaneous overlay of the red and green channels reveals punctate areas of co-localization (lower, right panel). The bright areas indicated by arrows are points of intense staining around the plasma membrane. Matched isotype antibody controls are shown in the lower, left panel are negative.

Figure 8:
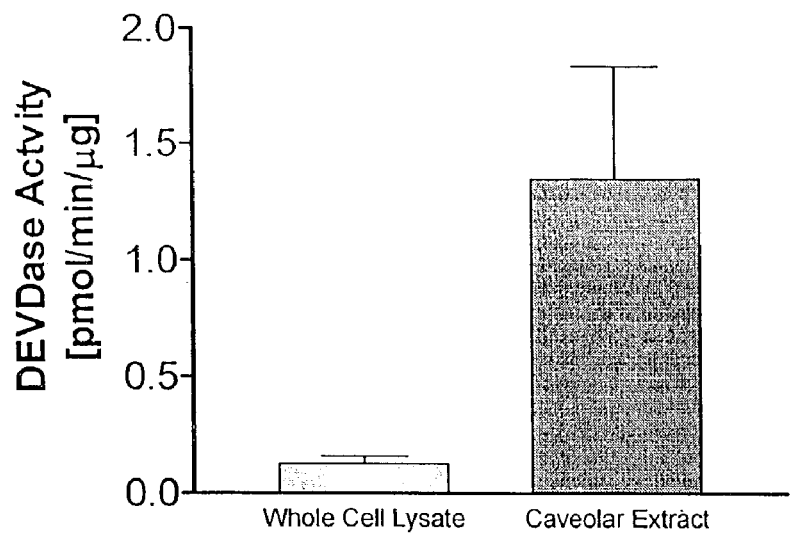
FIG. 8 shows a measurement of caspase-3 activity in caspase-containing fractions isolated from whole cell lysates by density gradient centrifugation (n=6). Activity is determined by p-nitroaniline absorbance at 405 nm following cleavage from a substrate peptide sequence DEVD. The reversible inhibitor DEVD-CHO was used to confirm caspase-3 specificity.

Caspase-3 containing caveolar fractions possess aspartic acid-directed protease activity (FIG. 8). The specific activity is reported as 1.35+/−0.486 pmol/min/μg total protein. In the whole cell lysate, the specific activity is 0.127+/−0.033 pmol/min/μg total protein. This clearly demonstrates the enrichment of active caspase-3 enzyme in the low-density cellular fractions.

Figure 9:
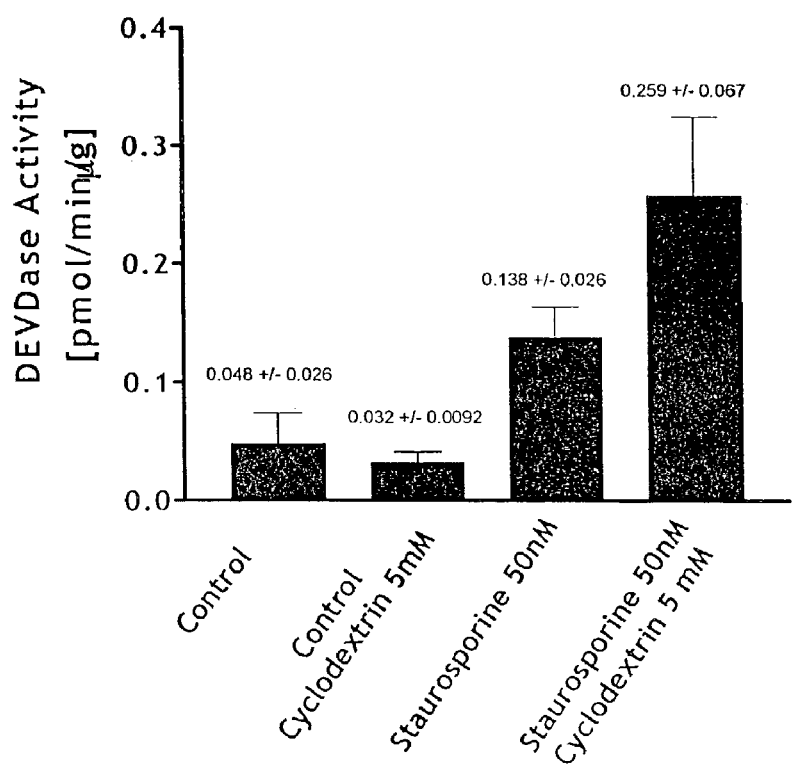
FIG. 9 shows measurement of caspase-3 activity in staurosporine-treated cells in the presence and absence of b-methyl-cyclodextrin pretreatment. Control cells received 0.05% DMSO final as a control for drug vehicle (n=4). Clarified supernatants from detergentsolubilized cells are assayed for DEVDase activity using the colorimetric caspase-3 substrate DEVD-pnitroaniline.

The physical proximity of caspase-3 and caveolae is necessary for appropriate transduction of a death signal. The sequestration of cholesterol from the plasma membrane can disrupt the localization of proteins within caveolae and lipid rafts, which has shown to interrupt signaling pathways. Staurosporine can induce caspase-3 activity in near-confluent monolayers of endothelial cells in culture (FIG. 9). Interestingly, the pretreatment of cells with β methyl-cyclodextrin enhances enzymatic activity.

Figure 10:
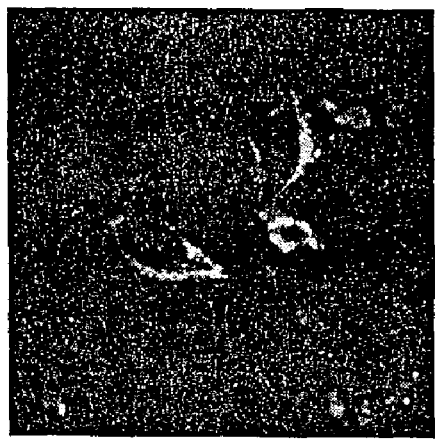
FIG. 10 shows phiPhiLux fluorescence of staurosporine treated endothelial cells+/− cyclodextrin or fillipin III. Punctate, localized fluorescence indicating staurosporine-induced caspase-3 activity detected near the plasma membrane (upper panels). Pretreatment of cells with cyclodextrin (lower, left panel) or fillipin III (lower, right panel) results in diffuse intracellular caspase-3 activity.
Figure 10:
Figure 10:
Figure 10:
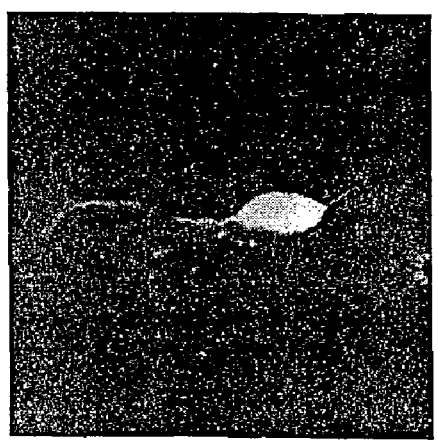

Using a fluorescent substrate, caspase-3 activity can b e visualized in intact cell preparations. Endothelial cells treated with staurosporine for 3 hours display punctate fluorescence (FIG. 10). Under similar conditions, cells exposed to cholesterol-altering agents such as b-methyl-cyclodextrin or fillipin III possess global diffuse fluorescence throughout the cells.

Discussion

Basic studies of the organization of signal transduction in cells have exploded in recent years with our evolving knowledge of caveolar microdomains. Indeed, it is of interest to recall the first subcellular description of compartmentation of receptor-signaling contributed nineteen years ago and find that the best explanation for the basis of this compartmentation lies in the organization of microdomains. It is, in fact, unlikely that one can over-state the importance of caveolae given the ever increasing number of receptors and effector molecules that are either contained within or interact with caveolae.

While a role for apoptosis exists in normal cardiovascular development, it is also recognized as a pathological step in cardiac diseases such as myocardial infarction, ischemia/reperfusion injury, and atherosclerosis. In addition, normal vascular growth and regression involves endothelial apoptosis, as do the required changes in endothelial growth that accompany the development of blood supply recruited by solid tumors. Dysregulation of endothelial apoptosis may disrupt the smooth intimal layer of blood vessels thereby promoting plaque formation. Given the critical role of endothelium in health and disease, it is reasonable to conduct studies aimed at furthering an understanding of the signaling mechanisms underlying endothelial apoptosis as they will likely lead to improved therapeutic interventions. Furthermore, nucleoside diphosphate kinase-B activity and thus, ecto-ATP generation by the breast cancer cell is associated with metastasis of human breast cancer and that blocking nucleoside diphosphate kinase-B prevents angiogenesis thus providing the basis of prophylactic treatment of breast cancer metastasis.

Figure 11:
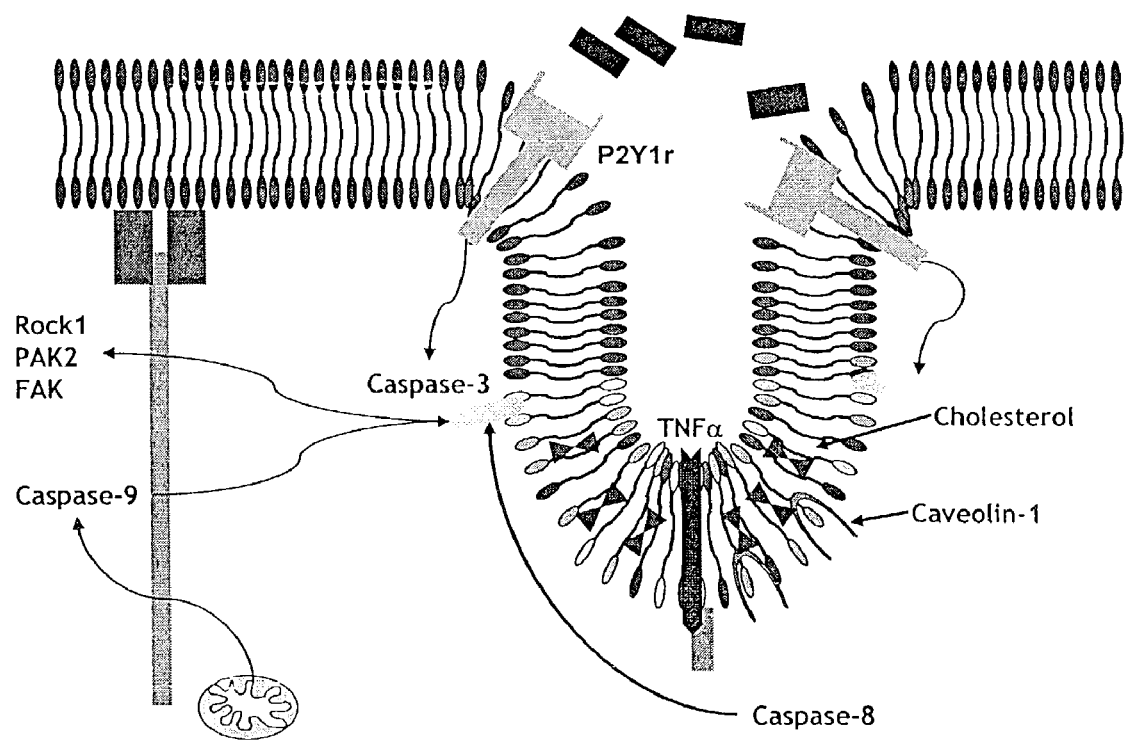
FIG. 11 shows a hypothetical model showing the targeting of caspase-3 by caveolae to specific plasmalemmal-localized substrates and its activation by P2Y1 receptor. The signaling of caspase-3 by receptors associated with the metastatic process and its putative prevention by the anti-angiogenic nucleoside diphosphate kinase-B inhibitors discovered in this project hold promise for prophylactic therapies for those at serious risk of developing breast cancer and breast cancer metastases.

Using guinea pig cardiac endothelial cells sorted by flow cytometry using PECAM-1 (CD31$^+$), grown in culture for two passages to expand cell number, and sonicated in non-detergent alkaline buffer, we have found that caspase-3 proenzyme (32 kDa) and its activated isoform (17 kDa) co-purifies with caveolin-enriched microdomains. In addition, immunofluorescent staining reveals co-localization of caspase-3 and caveolin-1 near the plasma membrane in whole cells. The confinement of a caspase-3 at the plasma membrane may be necessary for placing the active enzyme near a specific membrane-bound or membrane-associated substrate (FIG. 11). The localization of caspase-3 to other intracellular compartments would no doubt subserve a similar purpose for other enzymatic targets. Within the context of apoptotic mechanisms, microdomain signaling would result in a highly specific, physically constrained signal transduction pathway preventing undesired proteolysis from occurring.

Staurosporine engages the apoptotic machinery via intracellular pathways associated with the mitochondria. The resulting increase in mitochondrial permeability leads to the release of cytochrome C and the subsequent activation of caspase-9 through the formation of the apoptosome. Active caspase-9 cleaves and thereby activates caspase-3 leading to the degradation of cellular proteins involved in the maintenance of cellular homeostasis and structure. The depletion of plasma membrane cholesterol would not likely alter the components of this biochemical pathway upstream of caspase-3 activity.

The free movement of caspase-3 within the plasma membrane could prevent its regulated activation by initiator caspases. Alternately, caveolar disruption could eliminate the spatial association of caspase-3 with substrates at or near the plasma membrane. Either notion would result in the absence of complete, efficient proteolysis of proteins that might be necessary for apoptotic mechanisms such as membrane blebbing. However, this data suggests the localization of caspase-3 in caveolae may serve to inhibit its activation by initiator caspases in the absence of a death signal. Alterations in cholesterol content would allow for the translocation of caspase-3 away from caveolae. This results in enhancement of enzymatic activity as well as enables caspase-3 to display promiscuous characteristics. The diffuse staining pattern seen in cholesterol-altered cells is evidence of such promiscuity. Yet "intact" cells display punctate caspase-3 activity, which has been proposed to indicate early, low-level protease activation.

Figure 12:
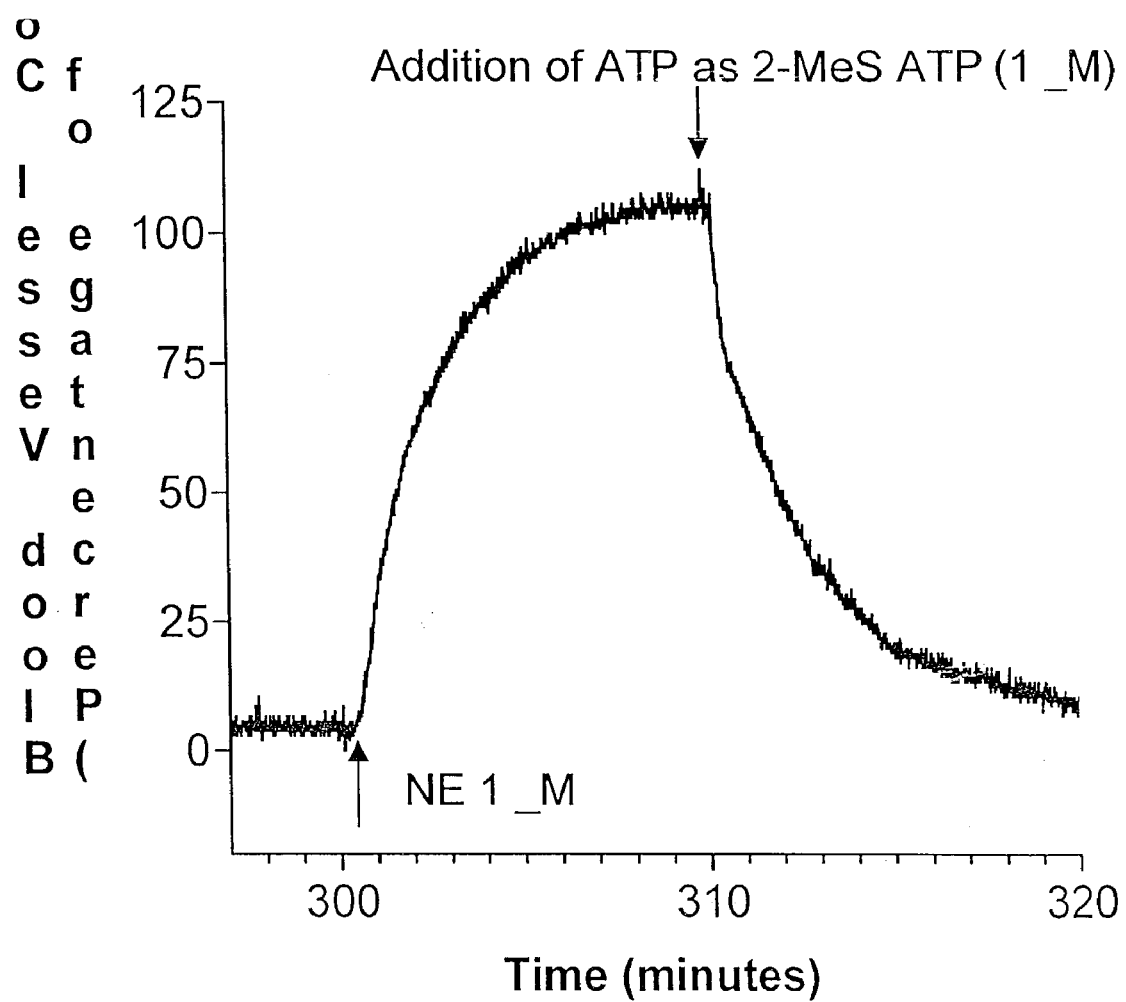
FIG. 12 shows that the addition of the ATP congener 2-methyl thio-ATP completely relaxes a norepinephrine contracted aorta (guinea pig).

Normal mammalian endothelial cells (EC) are known to respond to nucleotides such as ATP by initiating relaxation of the blood vessel FIG. 12). This relaxation contributes to the moment-to-moment regulation of blood flow by increasing sheer stress locally which further contributes to maintaining the extracellular presence of nucleotides in the blood stream by directly stimulating EC to release ATP. This released purine nucleotide in turn stimulates release of nucleotide down stream at adjacent endothelium via the P2Y1 receptor thus maintaining the increase in blood flow. EC release of ATP following increases in shear stress or activation by hormones such as bradykinin (BK) signals endothelial NO release and this effect is propagated by ATP acting on adjacent endothelium (American Journal of Physiology 281: H1657-H1666, 2001). Such a normal mechanism of blood-flow regulation is taken advantage of by cancer cells by secretion of nucleoside diphosphate kinase which supports both intravasation and extravasation of cells into and out of the blood stream by artificially raising purine levels.

The assumption that cancer cells utilize this pathway is supported by our recent data in guinea pig thoracic aorta suspended in an organ bath apparatus for measurement of tension, addition of the sympathetic neurotransmitter norepinephrine (NE) leads to a typical and expected contraction that is stable over time (see FIG. 12; NE response).

Figure 13:
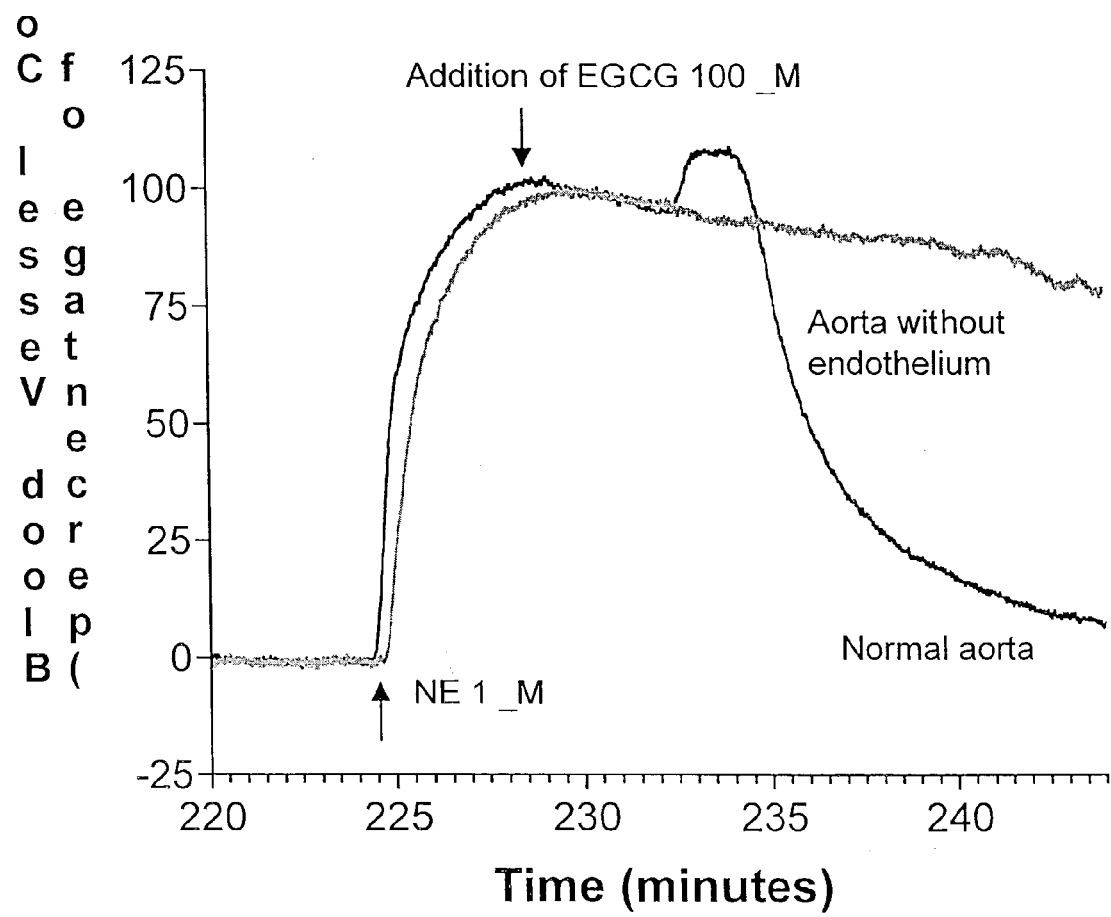
FIG. 13 shows the effects of epigallocatechin gallate lead to dramatic relaxation of the blood vessel pre-contracted with norepinephrine and are dependent on the presence of endothelium.

Addition of the eNDPK inhibitor epigallocatechin gallate (EGCG) at peak contraction leads to a further small contraction of the vessel followed by relaxation (FIG. 13) that is endothelium dependent. This effect of epigallocatechin gallate was unexpected since under these experimental conditions, purine nucleotides are not expected to accumulate. This relaxation may be due to direct effects of epigallocatechin gallate on the endothelial cells. This ability of epigallocatechin gallate to relax the vessel is dose-dependent and both contraction and relaxation are lost in the absence of endothelium.

Pretreatment of vessels with the nitric oxide synthase inhibitor nitro L-arginine methylester (L-NAME) blocks epigallocatechin gallate-dependent relaxation supporting the conclusion that endothelial cells release of nitric oxide subserves the relaxation. While the precise endothelium-dependent mechanism subserving epigallocatechin gallate-dependent contraction of vascular muscle is still under investigation, these experiments support a potential therapeutic role of the polyphenolic catechin gallates as relaxants of normal blood vessels as might be advantageous in treatment of hypertension. Furthermore, these results are consistent with the ability of human breast cancer cells to move in the blood stream due, in-part, to their ability to produce ATP.

This data suggests the possibility that while polyphenolic catechin gallates may prevent cancer cells from generating extracellular purines on their own and thus can limit their passage into and out of blood vessels, direct effects of these compounds may positively influence blood flow to areas of tumor as is the need in the case of efforts to bring sufficient concentrations of chemotherapeutic compounds to areas of tumor.

Additional studies aimed at direct analysis of the ability of polyphenolic catechin gallates to prevent breast cancer cell entry into and exit from vessels has been addressed by examining the ability of tumor cells to induce paracellular passages in endothelial cells monolayers in culture. Human endothelial cells grown to confluence in culture can be examined as a model of capillary intravasation or extravasation as in cases of human breast cancer metastasis in vivo, by examining their ability to form large (>30 µm) holes between cells (paracellular holes). Control cultures exhibit electrical capacitance and limit the passage of dyes across the monolayer. Addition of tumor cells on top of the monolayer at concentrations of 1 cancer cell per 10,000 endothelial cells leads to the widespread appearance of large paracellular holes in the monolayer within 15 minutes of application of tumor cells. Addition of normal breast epithelial cells does not produce this effect. Addition of epigallocatechin gallate at concentrations from 1 to 100 μM at the same time as application of the tumor cells prevents the formation of the paracellular passages in a dose-dependent fashion. The effect is complete at 30 μM epigallocatechin gallate. Careful quantification of the presence of paracellular holes is underway using video imaging. Preliminary results suggest that the direct effects of epigallocatechin gallate are consistent with their actions in vivo to prevent cancer cell metastasis.

The following references were cited herein:
1. Miller et al., J Clin. Oncol. 19:1195-1206 (2001).
2. Bange et al., Nat. Med. 7:548-552 (2001).
3. Steeg et al., J. Natl. Cancer. Inst. 80:200-204 (1988).
4. De la Rosa et al., Bioessays 17:53-62 (1995).
5. Hamby et al., Int. J. Cancer. 88:547-553 (2000).
6. Easty et al., Br. J. Cancer. 74:109-114 (1996).
7. Cao and Cao, Nature 398:381 (1999).
8. Yang et al., Circ. Res. 74:401-407 (1994).
9. Zhang et al., Science 276:1268-1272 (1997).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting tumor cell angiogenesis in a human tumor expressing and secreting nucleoside diphosphate kinase-B, comprising the steps of: a) identifying a human patient having a tumor, the cells of which express and secrete nucleoside diphosphate kinase-B; and b) contacting said cells of such a tumor with an inhibitor of the activity of nucleoside diphosphate kinase-B, wherein the inhibitor of nucleoside diphosphate kinase-B comprises ellagic acid.

2. The method of claim 1, wherein said cells are breast, lung, colon or prostate cancer cells expressing and secreting nucleoside diphosphate kinase-B.

3. The method of claim 2, wherein said cells are breast cancer cells expressing and secreting nucleoside diphosphate kinase-B.

4. The method of claim 2, wherein said cells are lung cancer cells expressing and secreting nucleoside diphosphate kinase-B.

5. The method of claim 2, wherein said cells are prostate cancer cells expressing and secreting nucleoside diphosphate kinase-B.

* * * * *

UNITED STATES PATENT AND TRADEMARK OFFICE
CERTIFICATE OF CORRECTION

| | | |
|---|---|---|
| PATENT NO. | : 7,678,549 B2 | Page 1 of 1 |
| APPLICATION NO. | : 10/331375 | |
| DATED | : March 16, 2010 | |
| INVENTOR(S) | : Buxton | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1926 days.

Signed and Sealed this

Fifteenth Day of February, 2011

David J. Kappos
*Director of the United States Patent and Trademark Office*